US006308747B1

(12) United States Patent
Farris

(10) Patent No.: US 6,308,747 B1
(45) Date of Patent: Oct. 30, 2001

(54) NEEDLELESS METHOD AND APPARATUS FOR TRANSFERRING LIQUID FROM A CONTAINER TO AN INJECTING DEVICE WITHOUT AMBIENT AIR CONTAMINATION

(75) Inventor: Barry Farris, P.O. Box 1817, Zephyr Cove, NV (US) 89948

(73) Assignee: Barry Farris, Zephyr Cove, NV (US)

( * ) Notice: Subject to any disclaimer, the term of this patent is extended or adjusted under 35 U.S.C. 154(b) by 0 days.

(21) Appl. No.: 09/165,026

(22) Filed: Oct. 1, 1998

(51) Int. Cl.[7] .................................................... A61M 5/00
(52) U.S. Cl. ............................ 141/25; 222/95; 222/107; 222/541.6; 222/541.9
(58) Field of Search ......................... 222/95, 107, 541.6, 222/541.9; 141/25–27

(56) References Cited

U.S. PATENT DOCUMENTS

| | | | | |
|---|---|---|---|---|
| 829,178 | | 8/1906 | Stegmaier . | |
| 1,377,113 | * | 5/1921 | Boyle | 222/107 |
| 2,486,321 | | 10/1949 | O'Sullivan . | |
| 2,773,521 | * | 12/1956 | Persson | 141/25 |
| 3,187,966 | | 6/1965 | Klygis . | |
| 3,419,007 | | 12/1968 | Love . | |
| 3,977,553 | | 8/1976 | Cornett, III et al. . | |
| 4,046,145 | | 9/1977 | Choksi et al. . | |
| 4,130,117 | | 12/1978 | Van Eck . | |
| 4,163,509 | * | 8/1979 | Amneus | 222/95 |
| 4,213,456 | | 7/1980 | Böttger . | |
| 4,465,472 | | 8/1984 | Urbaniak | 206/484 |
| 4,506,793 | | 3/1985 | MacGregor et al. . | |
| 4,643,309 | | 2/1987 | Evers . | |
| 4,883,473 | | 11/1989 | Thomas . | |
| 4,921,137 | * | 5/1990 | Heijenga | 222/107 |
| 4,944,736 | | 7/1990 | Holtz . | |
| 4,995,519 | | 2/1991 | Rose . | |
| 5,018,646 | * | 5/1991 | Billman et al. | 222/107 |
| 5,035,689 | | 7/1991 | Schroeder . | |
| 5,261,881 | * | 11/1993 | Riner | 222/95 |
| 5,334,173 | | 8/1994 | Armstrong, Jr. . | |
| 5,356,406 | | 10/1994 | Schraga . | |
| 5,374,263 | | 12/1994 | Weiler . | |
| 5,409,125 | | 4/1995 | Kimber et al. . | |
| 5,716,346 | | 2/1998 | Farris . | |

FOREIGN PATENT DOCUMENTS

| | | |
|---|---|---|
| 0 324 257 | 7/1989 | (EP) . |
| 0 350 772 | 1/1990 | (EP) . |
| 2594-687-A | 8/1987 | (FR) . |

* cited by examiner

*Primary Examiner*—J. Casimer Jacyna
(74) *Attorney, Agent, or Firm*—Bernhard Kreten

(57) ABSTRACT

An ampule having flexible walls with a zone which is programmed to promulgate collapse. The ampule includes an opening that is adapted to dock with a fluid receiving device such as a syringe in air tight sealing engagement. The collapse of the ampule is engineered to occur before breaking the seal that exists between the opening of the ampule and the docking syringe luer tip to ensure sterile transfer of fluid without contamination, especially from ambient air.

2 Claims, 4 Drawing Sheets

NEEDLELESS METHOD AND APPARATUS FOR TRANSFERRING LIQUID FROM A CONTAINER TO AN INJECTING DEVICE WITHOUT AMBIENT AIR CONTAMINATION

FIELD OF THE INVENTION

The following invention relates generally to a method and apparatus for transferring fluid from a deformable ampule or vial into a syringe, injecting system (IS) or cannula without the need for a needle. More specifically, a male and female docking arrangement is disclosed coupled with structure for storing and transferring liquids so that the number of times needles are used in a medicating situation is kept to a minimum. The ampule has a structure which docks with the syringe, (IS) or cannula in a fluid tight sealing arrangement and the ampule is designed to collapse easily when extracting a substance such as liquid therefrom so as to preserve the fluid tight seal and therefor not allow air into the ampule, or syringe, or injecting system during the collapsing phase.

BACKGROUND OF THE INVENTION

Diseases such as nosocomial infections, hepatitis and AIDS, which are pathogens that can be transmitted with the body fluids of a person, are running rampant globally. As a result, medical environments such as hospitals spend considerable amounts of money, time and energy attending to the problems that arise when hypodermic needles are required.

Complex protocols are evolving which attempt to minimize the likelihood of a needle stick from the time that a needle has been removed from its sterile storage environment through loading, utilization and disposal. Examples of heightened care with respect to the use of hypodermic needles are chronicled in patent literature, in the development of anti-stick needle caps, devices which destroy the needle itself after use and other instrumentalities for receiving both the used needle and syringe for safe disposal. Thus, the prevailing systems are based on the premise of the very existence of the needle for the medicating process.

The instant invention to a large extent obviates the need for the needles themselves in the many common instances where syringe needles have heretofore been used. Typically, one scenario where the use of a hypodermic needle is now commonplace includes the steps immediately prior to injection in the patient. The process involves loading the syringe with a sterile, pharmaceutical-grade fluid by extracting medicating fluid from a vial by using the affixed needle of a syringe for access. When using an ampule, the tip is broken off and then the ampule is entered with a needle, often a filtered needle to filter out glass particles. Next, the patient who is to receive this medicating fluid is injected with a new needle.

Prior art drug containing vials are formed from an open mouthed bottle or jar wherein the walls of the container defining the vial are rigid and non-flexible. The opening of the jar includes a lip which supports a metal ferrule which supports an elastomeric diaphragm made from a rubber-type material having a resealable property such that once the diaphragm has been penetrated by a needle and then removed, the diaphragm reseals itself. Examples of these devices are believed to be presently classified in class 604, subclass 415. Typically, a syringe body is first fitted with a hypodermic needle. It is common practice that prior to the needle being plunged into the vial through the rubber diaphragm, it is first loaded with ambient air. Because the prior art vials are rigid, the vial is first pressurized to assist in fluid withdrawal. While this technique makes it easier to withdraw fluid, it introduces non-sterile air into the vial. Technically, the needle is to then be replaced with a new needle prior to injecting a patient.

The syringe is, in general, an elongate cylindrical object having a plunger adapted to reciprocate within an interior hollow. By withdrawing the plunger from the interior of the cylindrical hollow, fluid is drawn from the vial and is loaded into the syringe. Once the syringe has been removed from the vial, great care must be exercised for a multiplicity of reasons. The medication contained within the syringe is now provided with the present ability to discharge the medication to any who come in contact with the needle, albeit inadvertently. In order to reduce the amount of time a "loaded" syringe is carried, the medicating healthcare professionals normally will use a cart which contains all pharmaceuticals which are to be distributed during rounds to the patients. This reduces the amount of time the healthcare professional is required to walk with an armed syringe whose needle has been exposed or whose exposed needle has been recapped. Recapping provides further risk of self sticking due to misaligning a needle cap with the syringe.

After dispensing the medicine to the patient, the healthcare professional typically has one of several choices, none of which is entirely satisfactory for safe disposal of the needle. In one scenario, the healthcare professional is required to carefully recap the needle hoping that in the multiple times this procedure is reperformed he or she does not misalign the cap with the needle and inadvertently suffer a needle stick.

Another device has been developed which appears like a pencil sharpener and allows the healthcare professional to place the leading end of the syringe into an opening where an electric current is applied to the needle which melts the needle.

A third strategy involves discarding the needle and the syringe in a container for subsequent destruction or internment as biomedical waste. This technique presents ongoing risk to people who subsequently handle this waste.

The Food and Drug Administration (FDA) has accordingly issued an alert urging hospitals to use needleless systems or recessed needle systems instead of hypodermic needles for accessing intravenous lines. Plastic cannulas now exist which can fit onto luer connections and penetrate sealable diaphragms on infusion catheters. Thus, the FDA is urging the use of hypodermic needles only to penetrate the skin.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

U.S. PATENT DOCUMENTS

| U.S. PAT. NO. | ISSUE DATE | INVENTOR |
|---|---|---|
| 829,178 | August 21, 1906 | Stegmaier |
| 2,486,321 | October 25, 1949 | O'Sullivan |
| 3,187,966 | June 8, 1965 | Klygis |
| 3,419,007 | December 31, 1968 | Love |

-continued

| | | |
|---|---|---|
| 3,977,553 | August 31, 1976 | Cornett, III et al. |
| 4,046,145 | September 6, 1977 | Choksi, et al. |
| 4,130,117 | December 19, 1978 | Van Eck |
| 4,213,456 | July 22, 1980 | Böttger |
| 4,465,472 | August 14, 1984 | Urbaniak |
| 4,643,309 | February 17, 1987 | Evers |
| 4,944,736 | July 31, 1990 | Holtz |
| 5,035,689 | July 30, 1991 | Schroeder |
| 5,334,173 | August 2, 1994 | Armstrong, Jr. |
| 5,356,406 | October 18, 1994 | Schraga |
| 5,374,263 | December 20, 1994 | Weiler |
| 5,409,125 | April 25, 1995 | Kimber, et al. |
| 5,716,346 | February 10, 1998 | Farris |

FOREIGN PATENT DOCUMENTS

| PATENT NO. | ISSUE DATE | INVENTOR |
|---|---|---|
| FR 2594-687-A | August 28, 1987 | Hosnedl |
| EP 0 324 257 | July 19, 1989 | Smiths Industries |
| EP 0 350 772 | January 17, 1990 | Hansen |

Evers (see for example FIGS. 3 or 6) only connects with a syringe because its "container (1) is provided with an outlet opening (2) having a surface in the form of an outwardly widening truncated cone" (see column 2, lines 27–29).

When the Evers device is installed on a syringe tip the vial (1) must first be axially advanced to the right of the Evers right-hand side drawing. This causes a radial force by distending the outwardly widening truncated cone (2). Once the axial force is no longer applied, there is still a tendency or a reaction of the plastic material forming the outwardly widening truncating cone (2) to return to its original unstressed configuration. Since the cone is acting on a surface which is canted with respect to the long axis of the vial, the surface has a force component parallel thereto which encourages the vial to slide off from the syringe. Evers featured a second embodiment (FIG. 6) wherein the opening "has been provided with peripherally arranged interior annular grooves across the outlet direction. Grooves of this kind apparently give improved sealing for the syringe tip (8) especially if the outlet opening is made of very thin and flexible plastic material." (Column 3, lines 4–8.)

Kimber, et al. provides a neck portion (3) (FIGS. 2 and 5), but this is not the area of frangibility. Fracture occurs above the neck portion at outlet opening (7) and threads are located in the area between the opening (7) and the neck portion (3). These threads are intended to coact with the internal threads (15) carried on the peripheral wall (12) of a conventional luer coupling on the syringe. The threads are advanced until they bottom out against a bottom wall (13) on the luer coupling.

Holtz teaches the use of a cap interposed between the syringe and the vial. Holtz, column 3, lines 32, et seq. states "since the cap (5) makes the assembled bottle and adapter (1) completely sealed and caps (12) and (14) make the syringe completely sealed these two assemblies may be carried loose . . . with no fear of contamination . . . ". Thus, the cap (5) and adapter (1) remain with the vial while the caps (12) and (14) remain with the syringe.

Stegmaier teaches the use of a cap tailored to never be reinstalled so as to prevent the bottle from being refilled. Thus, the portion that has indicia thereon includes a frangible section which precludes and "obviates the likelihood of refilling" (column 1, lines 10–11). Thus, once the cap has been removed from the bottle, it is never possible to be reattached. Thus, any indicia on the cap has limited value because it cannot be reassociated with the syringe that contains the contents heretofore in the vial.

Hansen teaches a vial constructed to more easily remove the tab, allowing access to the vial's interior.

SUMMARY OF THE INVENTION

This invention chronicles further efforts by the applicant enhancing U.S. Pat. No. 5,716,346.

By way of contrast, applicant's invention differs markedly from the foregoing. The vial 10 includes a tapering section 8 which converges to an opening 12. When this convergent end (and its circular profile) runs over the cone shaped luer end of the syringe, it is distorted and distended. As it approaches an annular outer wall of the luer coupling it wedges between the annular wall and the cone of the syringe tip. The vial collapses during emptying, assuring no ambient air contamination.

The instant invention completely avoids the use of a needle when extracting fluid from a vial or ampule. In its essence, the instant invention takes advantage of a coupling that is the standard on a majority of syringes which had heretofore only been used in the past to support the hypodermic needle on the syringe. This coupling, called a luer fitting, has a male component and a female component. Typically, the syringe is configured with the "male" luer coupling which appears as a truncated cone that has an opening at its narrowest cross section. The luer coupling diverges toward an interior cylindrical hollow portion of the syringe. The instant invention replaces the "female" luer coupling and associated needle itself and instead replicates the female coupling on a specially formed ampule or vial so that docking between the ampule and a needleless syringe benefits from the pre-existing male coupling already found on common syringes. Walls of the ampule or vial are flexible to promote removal of the fluid therewithin.

The walls of the ampule are further tailored to promulgate collapse in a preordained manner. This collapse occurs by forming the ampule with a shape that provides a force gradient along the outer skin of the ampule when liquid is extracted beyond the fluid tight connection with the syringe.

With an opening of the ampule and the opening of the syringe in face-to-face docking registry and in fluidic communication, the ampule can be evacuated by any of a combination of manipulative steps. First, assume the syringe is in its initialized state, with its plunger nested well within the cylindrical hollow of the syringe body so that the plunger is in a compact, retracted state. The contents of the ampule can then be transferred with a negligible amount of air bleed at the ampule/syringe interconnection by deforming the side walls of the ampule and "milking" (i.e. applying hydrostatic force to) the liquid through the ampule walls and thus into the syringe. This causes the plunger of the syringe to translate along the cylindrical hollow. As the plunger advances along the cylindrical hollow, liquid enters the syringe.

Another strategy involves manipulation of the plunger to draw the fluid from the ampule by suction so that the filling of the syringe occurs by retracting the plunger to extract the liquid from the ampule while collapsing the ampule. The ampule is specially constructed to collapse. As before, the plunger starts well within the syringe and reciprocates outwardly of the cylindrical hollow.

A third strategy is a hybrid of the two previously discussed techniques which involves manipulation of both the ampule by (1) squeezing the ampule and suction by (2) moving the plunger out of the syringe cylindrical hollow.

Thereafter, the ampule may be disconnected from the syringe for syringe deployment.

Once the ampule has been removed, a syringe has the intended fluid medication disposed therewithin. Unlike the prior art, no needle has yet been involved. Also, no air from the ambient environment has been mixed with the sterile fluid as was the case with prior art rigid wall vials. The seal between the syringe and ampule, coupled with ampule wall deformation excludes ambient air.

In one form of the invention, it is contemplated that the opening associated with the ampule is provided with a removeable cap having a luer-type coupling and an indicia bearing tab. The volume and medicinal contents of the ampule is stamped on the tab for identification purposes. With such an arrangement, it is possible to transfer the cap and tab from the ampule and connect the cap to the syringe to provide a tell tale of the contents of the fluid contained within the syringe. As an alternative, the ampule could remain docked to the syringe until subsequent use. The ampule would also note its contents on a surface thereof.

As a result of this system, the entire process for filling a syringe has been accomplished without the use of a needle. Personnel are able to operate more quickly with less fear of either inadvertent needle stick or inadvertent exposure to the medicine contained within the syringe.

It is to be noted that for many in-patients, the standard procedure in a hospital is to tap into a person's vein only once with an infusion catheter and to leave the catheter needle in place with tubing communicating therewith so that subsequent fluids such as intravenous drips and the like can be used. With such a system, a needle would never be needed with the syringe according to the present invention. "Y" connectors are well known in the art, one branch of which would have a complemental female luer coupling. Thus, for a patient's entire stay at a hospital, the only needle associated with that one patient, ideally, would be the one which initially had been placed in the patient's vein to support the infusion catheter. In this way, the opportunity for inadvertent needle sticks would be reduced to an absolute minimum.

The instant invention is further distinguished over the known prior art in that zones of programmable deformation are strategically provided which encourage collapse of the body of the ampule with less pressure than has been heretofore experienced. By providing this important feature, it is possible to provide wall thickness which can be somewhat thicker while still affording the same ability of the walls of the ampule to collapse on itself. The interplay of the present invention is between the sealing forces that exist between the docking of the syringe and the ampule. This sealing force should be as high as possible while providing the thickest wall possible on the ampule and still allow easy collapse of the ampule. By having a relatively thicker wall, the ampule is more robust and provides a further impediment to transpiration through the wall of the ampule. An ancillary benefit is that the criticality of the wall thickness during blow, fill, seal (BFS) manufacture has been lessened.

OBJECTS OF THE INVENTION

Accordingly, it is a primary object of the present invention to provide a method and apparatus for transferring sterile fluid from an ampule to a hypodermic syringe without the need of a hypodermic needle.

It is a further object of the present invention to provide a device and method as characterized above which reduces the amount of time which hospital staff must spend in transferring fluid from a sterile ampule to a hypodermic syringe while also eliminating the fear of an inadvertent needle stick thereby avoiding the possibility of both unwanted contamination and unwanted medication.

A further object of the present invention contemplates providing a device and method as characterized above which is extremely inexpensive to fabricate, safe to use and lends itself to mass production techniques.

A further object of the present invention is to provide a device which can reduce the number of times that needles are required in a hospital or other medical setting.

A further object of the present invention contemplates providing a device and method which minimizes the disposal problems of hypodermic syringes with needles.

A further object of the present invention contemplates providing a device and method for use in which a telltale is associated with first the ampule that stores the medicine, and then the syringe so that the fluid transferred from the ampule and into the syringe will be known at all times. In this way, the chain of custody of the fluid can be more readily monitored.

A further object of the present invention contemplates providing a system for loading syringes that obviates the need for the medicating health professional from having to trundle a miniature pharmacy on a cart from patient to patient. By pre-filling the syringes at a remote location added security and efficiency may be provided.

A further object of the present invention is to provide a programmed ampule wall structure that promulgates collapse before the seal that exists between the ampule and the syringe or other fluid receiving device admits air therein.

When viewed from a first vantage point it is an object to provide a needleless dosage transfer system for removing a sterile fluid from a sealed vial to a conventional syringe. The syringe has a plunger such that the plunger of the syringe translates from a first position telescoped within an interior cylindrical hollow of the syringe to a second position where the plunger has been displaced from the interior hollow and replaced by the fluid. The vial is defined by an end, collapsible sidewalls extending from the end thereby defining a blind bore and having an open end, a coupler at the open end of the vial, and a removable cap occluding the open end at the coupler. The vial coupler is provided with means to connect to a needleless opening of the syringe to be in fluid communication therewith, whereby fluid can be transferred to the syringe from the vial without an interconnecting needle.

Viewed from a second vantage point, it is an object to provide a method for transferring injectable fluids from a storage ampule or vial to a needleless syringe or other injecting device using a male luer fitting or other fitting. The syringe has a first coupling and an opening which communicates within an interior cylindrical hollow of the syringe so that fluid passes by the first coupling through the opening and into the hollow to load the syringe. The steps include providing a vial filled with fluid and with an outlet which has a second coupler defining the outlet. The vial is sealed by occluding the coupler outlet with a cap. Subsequently, removing the cap and orienting the first and second couplers into complemental fluid tight docking arrangement (so that the opening of the vial registers with the opening of the syringe) allows transfer of the contents of the vial to the syringe without the need for a traditional needle extraction system.

Viewed from a third vantage point, it is an object to provide a method for forming an ampule to transfer medicine to be injected. The steps include forming an ampule with resilient walls so that the ampule can be collapsed, forming an opening on the ampule such that the opening is circumscribed by a coupler which is fashioned to receive a dose administering device, filling the ampule with the medicine and finally capping the ampule opening.

Viewed from a fourth vantage point, it is an object of the present invention to provide an ampule having a body with means to promulgate the body's collapse and a cap connected to the body and an opening at a scoreline between the body and the cap.

Viewed from a fifth vantage point, it is an object of the present invention to provide a method for transferring liquid from an ampule into a dosing device including the steps of: forming the ampule with the liquid by blow, fill and sealing; forming the ampule with a severable cap; and forming a body of the ampule with a zone of preprogrammed deformation to collapse upon liquid extraction.

These and other objects were made manifest when considering the following detailed specification when taken into conjunction with the appended drawing figures.

DESCRIPTION OF PREFERRED EMBODIMENTS

Figure 2:
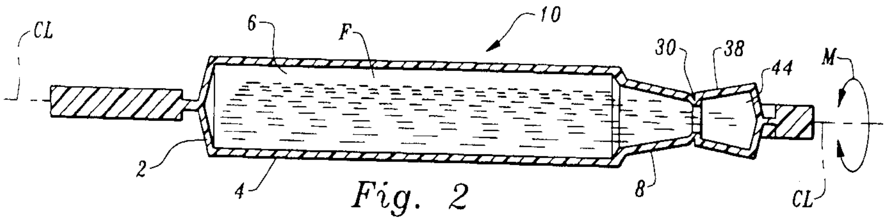
FIG. 2 is a sectional view longitudinally of the ampule.

Referring to the drawings now, wherein like reference numerals refer to like parts throughout the various drawing figures, reference numeral 10 is directed to the vial or ampule according to the present invention.

Figure 1:
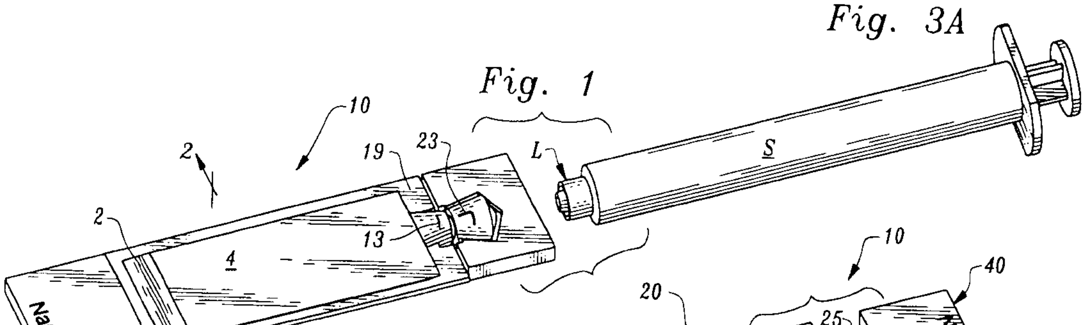
FIG. 1 is a perspective view of the ampule according to the present invention prior to docking with a fluid receiving device such as a syringe.
Figure 4:
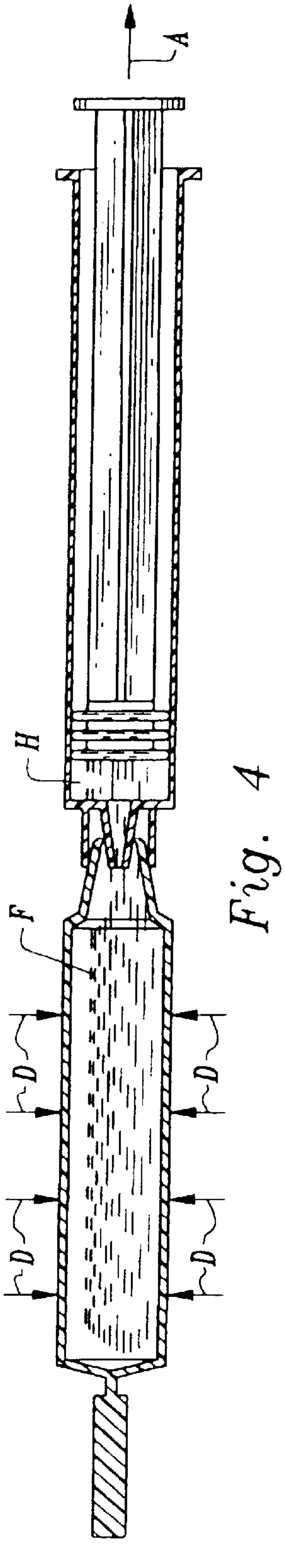
FIG. 4 is a sectional view of the ampule docked with the fluid receiving device shown section.
Figure 5:
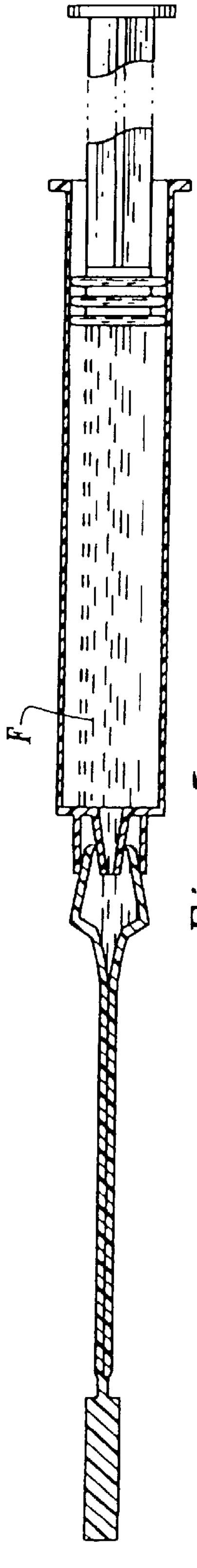
FIG. 5 is a view similar to FIG. 4 showing the collapse of the ampule upon the extraction of the fluid therewithin into the syringe.
Figure 7:
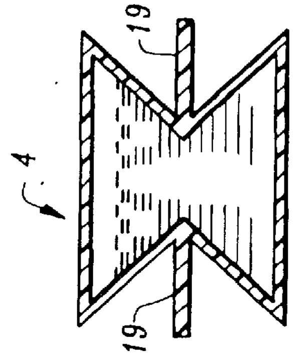
FIG. 7 is a sectional view of the cross-section of the ampule body according to one form of the invention according to a second variation of the invention.
Figure 7A:
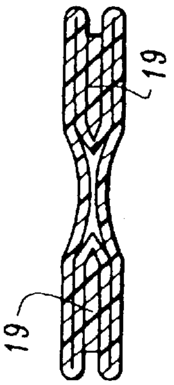
FIG. 7A is a view of that which is shown in FIG. 7 when the ampule is collapsed.

In its essence, the vial 10 is formed from two parts: a body portion 20 and a cap portion 40. An area of transition noted as a scoreline 30 serves as an area of demarcation between the cap 40 and body 20. The scoreline 30 allows the cap 40 to be dissociated from the body 20 so that the body 20 can dock with a syringe S as shown in FIGS. 1, 4 and 5 for filling the syringe S with a fluid F contained within the body 20 of the vial 10.

More specifically, and referring to the drawings in detail, the vial 10 includes a body 20 having an end wall 2, and an enclosing sidewall 4. The peripheral side wall 4 has one proximal end coterminus with an outer periphery of the end wall 2 and extends away from the end wall 2 so that a blind bore 6 has been formed within which the fluid F is to be stored.

Figure 4A:
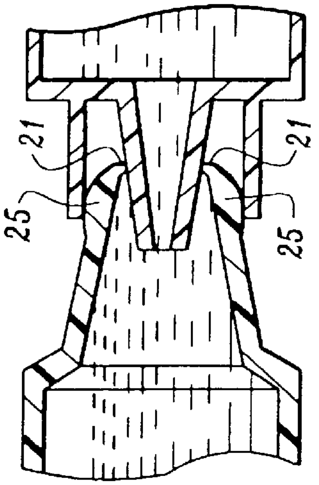
FIG. 4A is a sectional view detailing the locking of the ampule on the luer of the syringe.

Typically, fluids such as a saline solution, water for dilution and injection, heparin or pharmaceutical drugs and other medicaments can be stored within the blind bore 6. A distal end of the side wall 4 remote from the end wall 2 is provided with a tapering section 8 which converges away from the body 4 and towards a longitudinal axis CL of the vial 10 defining a converging portion of the vial 10. This tapering section 8 converges to an opening 12, or outlet and thereafter communicates with the cap 40. The opening 12 defines a coupler of the vial 10. The area of transition where the opening 12 is located is preferably coincident with the scoreline 30 to facilitate fracture of the vial 1 at the opening 12. Thus, the cap 40 can be separated from the body 20. After fracture (caused by shearing torsion—see M of FIG. 2), the plastic at the opening 12 tends to distort (forming a "chamfer" or "bevel") (FIG. 4A), forming a circular radially inwardly directed biting and/or sealing edge 21. The edge 21 enhances the seal with a luer on the syringe, injection system, cannula, etc.

The cap 40 includes a flag type tab 42 on an exterior surface thereof upon which is printed the product contained within the vial 10. The tab 42 is shown having a substantially rectangular, planar configuration to provide an exposed surface sufficient to place the name of the product on the tab. The tab 42 also serves as a purchase area to allow a person to grasp the cap 40 so that a twisting motion M of the cap 40 with respect to the body 20 will cause severing of the body 20 from the cap 40 at the scoreline 30.

The cap 40 also includes an interior passageway 44 having a diverging contour 38 which substantially mirrors the slope of the tapered section 8 of the body 20 of the vial 10 about an axis of symmetry coincident with the scoreline 30. This diverging passageway 44 extends a short distance within the cap 40 for purposes to be assigned.

Figure 3A:
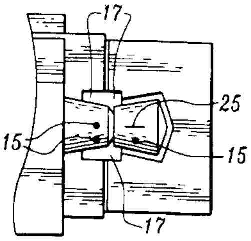
FIG. 3A is a plan view of the cap and ampule near thereto.
Figure 3:
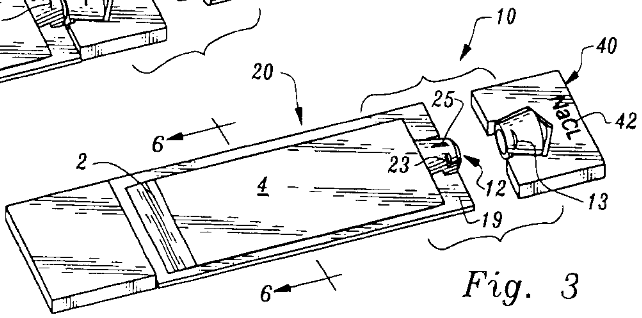
FIG. 3 is a perspective of the ampule.

As shown in FIG. 3, prior to docking with the empty syringe S (or IS or needleless cannula), the cap 40 will have been removed from the body 20 of the vial 10. This allows the opening 12 of the body 20 to be exposed. The opening 12 has an inner peripheral dimension complemental to an exterior diameter of a male luer coupling L found on the syringe's or IS's or cannula's outlet. This coupling L defines an opening which forms a coupler of the syringe. Typically, this luer-type connection tapers and diverges as it approaches a cylindrical hollow H of the syringe S. Some luer connections include a cylindrical collar which overlies all but a tip of the male luer coupling. The collar usually has an interior thread or female bayonet coupling.

For a friction fit, and with respect to the syringe S shown in FIG. 1, the taper of the luer L traditionally couples to a needle. In the present invention, the syringe docks with the vial 10 as shown in FIGS. 4 and 5 such that the "male" conical taper of luer coupling L of the syringe S passes within the female opening 12 of the body 20 and becomes frictionally engaged in the tapering section 8 of the vial's body 20. This connection may be enhanced by providing an exterior of tapering section 8 with a projection such as a male thread 13 (FIG. 1) or pip 15 (FIG. 3A) which enhances the force and sealing power the wall of opening 12 exerts on the luer L. A complemental "L"-shaped bayonet coupling 23, shown in FIG. 3, and/or a ramp 25 (FIGS. 3 and 4A) could also enhance the seal with the syringe S by wedging with the collar/luer tip. Further, cutout(s) 17 near opening 12 and on peripheral flashing 19 (which surrounds the ampule 10) can exert holding force to the interior and leading edge of the syringe collar.

Note that the plunger P on the syringe S (FIG. 4) is in a contracted position such that the syringe's cylindrical hollow H, located on an interior portion of the syringe S has received the plunger P to its entire extent and the push rod of the plunger P is in a position immediately adjacent to the cylindrical barrel of the syringe S. In other words, the syringe S is empty.

With respect to FIG. 5, it should be noted that the side walls 4 of the vial 10 are formed from a material having the ability to elastically deform in the presence of force. In other words, the side walls 4 of the body of the vial 10 is designed to collapse. In this way, fluid F contained within the vial 10 can be transferred into the syringe S without leaking appreciable fluid or bleeding contaminating ambient air into the system. It is contemplated that one of three methods could be used to transfer the fluid F of the vial 10 into the syringe S.

One scenario, shown in FIG. 4, envisions the vial 10 being deformed by providing external force in the direction of the arrows D along the outer periphery of the side walls 4. This causes the incompressible fluid F to be forced from the vial 10 and into the syringe S. The plunger P will now be forced by fluidic pressure, induced from the vial 10, to move the plunger P from a first contracted position (FIG. 4) to a second expanded position (FIG. 5). The cylindrical hollow H of the syringe S receives the fluid F. In other words, the syringe S will now have been filled with the fluid F and the plunger P will have been extended to a second position for delivery to a patient.

A second preferred scenario involves docking the syringe S or needleless cannula with the vial 10 as described above. Rather than exerting force D on the vial 10, instead the plunger P is pulled in the direction of the arrow A and causes negative pressure to exist in the cylindrical hollow H of the syringe S. Since the side walls 4 of the vial 10 are elastically deformable, the pressure induced by pulling the plunger P in the direction of the arrow A will cause the fluid F within the vial 10 to migrate into the cylindrical hollow H of the syringe S, filling the syringe S.

A third scenario involves a hybridization of the first two mentioned techniques. Namely, force D on the exterior side walls 4 of the vial 10 will be coupled in concert with pulling of the plunger P in the direction of the arrow A so that the incompressible fluid F will have migrated from the vial 10 to the syringe S.

Figure 15:
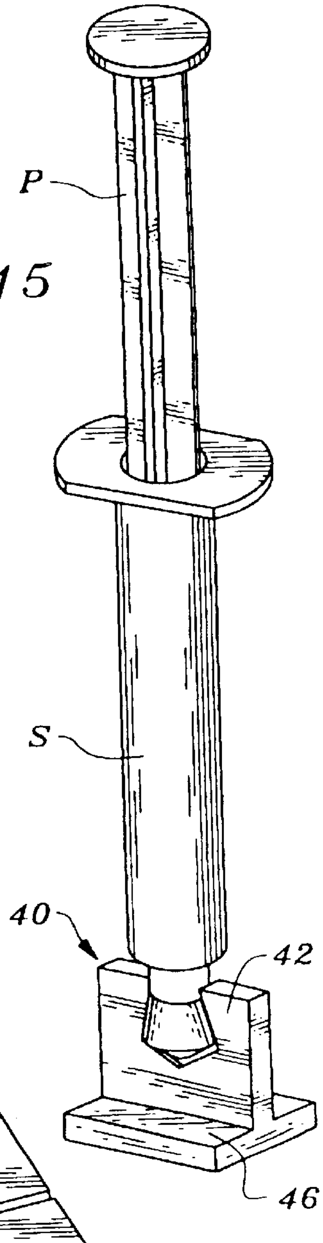
FIG. 15 shows the syringe connected to the ampule cap, standing on end.

FIG. 15 is directed to a final manipulation of one component of the apparatus according to the present invention. The cap 40 has indicia thereon correlative to the identity of the fluid F which has now been transferred from the vial 10 into the syringe S. FIG. 3 shows sodium chloride. The cap 40 has an interior passageway 44 and exterior contour 38 which mirrors the geometry of the ampule's conical section 8 and opening 12, perhaps including thread 13, dot(s) 15, "L"-shaped bayonet coupling 23 or ramp(s) 25. The cap 40 is placed in axial registry with and forced onto the luer of the syringe S or needleless cannula. Thus, the syringe S or cannula will be covered with cap 40. As mentioned above, the scoreline 30 of the opening 12 defines an axis of symmetry between the tapering section 8 of the vial body 20 and the diverging contour 38 of the passageway 44 of the cap 40. As shall now be evident; the cap 40 can be frictionally forced over the conical taper of the syringe S thereby covering the male luer coupling L.

In this way, after the syringe S is loaded and ready for subsequent use, the contents of the fluid F within the syringe S will be known to the person dispensing the medication. Thus, different fluids can be pre-loaded into several syringes in a secure area. The healthcare professional can merely take a collection of the syringes or needleless cannulas to the site for ultimate medicating without having to use a drug preparation cart as is commonly in vogue today. The cap 40 can include a support foot 46 to support the syringe S or vial 10 on end. The foot 46 is located at an end of the cap 40 remote from passageway 44 and defines a planar surface transverse to the long axis 2. This allows the on end orientation. The foot 46 is preferable faceted at extremities thereof so that the foot 46 prevents the syringe S or ampule 10 connected thereto from rolling when oriented as shown in FIGS. 1 and 5. Note the ampule 10 is also marked with its contents (e.g., sodium chloride, FIG. 1) and can also be used as a cap for the syringe by leaving the ampule 20 on the syringe S as in FIGS. 4 and 5.

As had been mentioned briefly hereinabove, many people receiving home care and in hospitals as in-patients have infusion catheters operatively coupled at all times during their stay. Many of the infusion catheters include a male luer coupling complemental to the contour of both the vial 10 and the passageway 44 of the cap. When this is the case, the syringe S never needs to include a needle on the male luer coupling L. Instead, one can administer the medicine directly through the infusion catheter. In this way, the number of instances where trained medical personnel are exposed to administering fluids with hypodermic needles will be minimal. This reduces the amount of time and care required in the efficient performance of their tasks and minimizes both occasions for needle sticks and problems of needle disposal.

Figure 6:
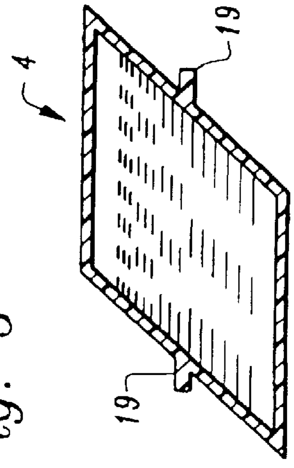
FIG. 6 is a sectional view of the cross-section of the ampule body according to one form of the invention.
Figure 6A:
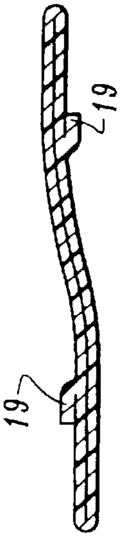
FIG. 6A is a view of that which is shown in FIG. 6 when the ampule is collapsed.
Figure 11:
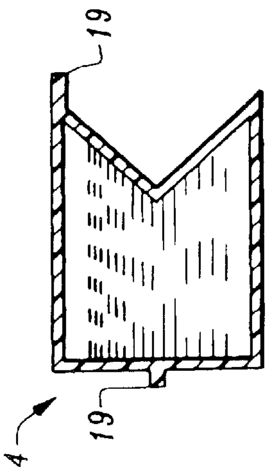
FIG. 11 is a sectional view of the cross-section of the ampule body according to one form of the invention according to a sixth variation of the invention.
Figure 11A:
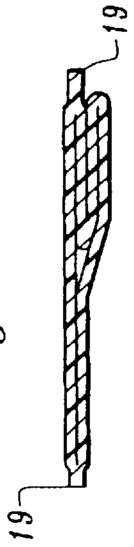
FIG. 11A is a view of that which is shown in FIG. 11 when the ampule is collapsed.
Figure 10A:
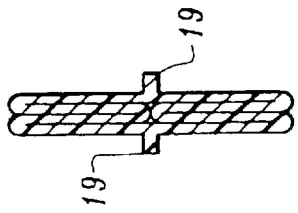
FIG. 10A is a view of that which is shown in FIG. 10 when the ampule is collapsed.
Figure 10:
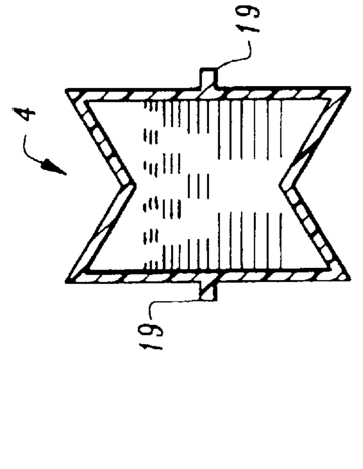
FIG. 10 is a sectional view of the cross-section of the ampule body according to one form of the invention according to a fifth variation of the invention.
Figure 9:
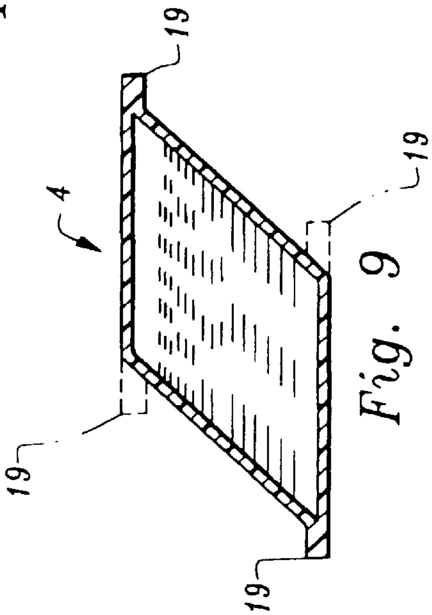
FIG. 9 is a sectional view of the cross-section of the ampule body according to one form of the invention according to a fourth variation of the invention.
Figure 9A:
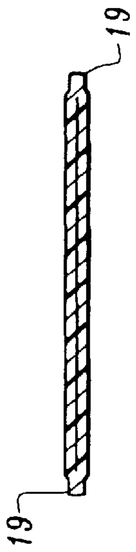
FIG. 9A is a view of that which is shown in FIG. 9 when the ampule is collapsed.
Figure 8:
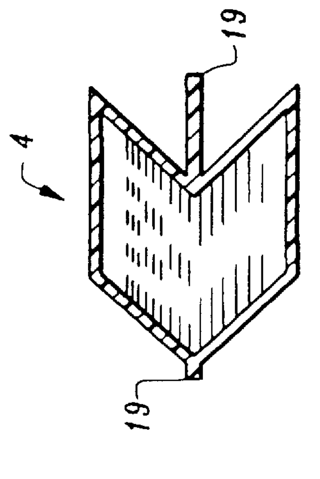
FIG. 8 is a sectional view of the cross-section of the ampule body according to one form of the invention according to a third variation of the invention.
Figure 8A:
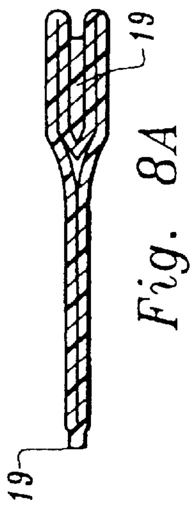
FIG. 8A is a view of that which is shown in FIG. 8 when the ampule is collapsed.
Figure 12:
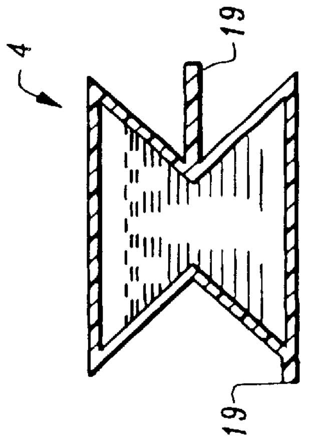
FIG. 12 is a sectional view of the cross-section of the ampule body according to one form of the invention according to a seventh variation of the invention.
Figure 12A:
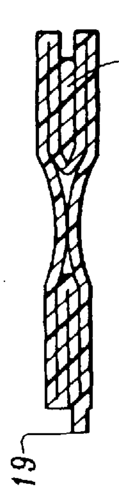
FIG. 12A is a view of that which is shown in FIG. 12 when the ampule is collapsed.
Figure 13:
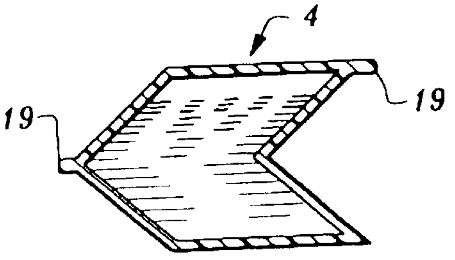
FIG. 13 is a sectional view of the cross-section of the ampule body according to one form of the invention according to a eighth variation of the invention.
Figure 13A:
FIG. 13A is a view of that which is shown in FIG. 13 when the ampule is collapsed.

FIGS. 6 through 13 show variations in the cross-sectional contour that the ampule 10 can assume and will further suggest to the reader other geometrical shapes which are intended to be included as part of this invention. They can all be characterized as having a static structure which yields in the face of the pressure shown in FIG. 4 either along the direction of the arrow "A" and/or pressure along the arrows "D" so that they can collapse from their expanded positions (FIGS. 6 through 13) to their collapsed configuration (FIGS. 6A through 13A). For example, the FIG. 6 version (also depicted in FIGS. 1 and 3) in section shows a parallelepiped type structure, namely a parallelogram in section which collapses more readily into the FIG. 6A configuration with less force than for example a structure which would be triangular in section. Surprisingly, the included acute angles on the parallelepiped structure of FIG. 6 need not be as severe as shown in the drawings. In fact, for a given wall thickness the included angle can be approaching 90°, but as the material that forms the exterior skin gets thicker, the angle can decrease accordingly. Whereas FIG. 6 shows the flashing 19 that exists when forming the devices in a blow, fill, seal machine, as being medially disposed upon the two parallel sidewalls, FIG. 9 shows the flashing 19 as being located at diametrically opposed corners. While the flashing 19 may be located as shown in FIG. 9 on the major diameter, the flashing could similarly be located on the minor diameter as shown in dotted lines. Again referring to FIG. 6, although the flashing 19 is located medially along two parallel sidewalls, they can be moved up or down along the length thereof or on the walls which are shown as being horizontal in FIG. 6. The key is to provide an area or a zone which promulgates deformation and to that end, all variations appear as polygonal in section with a least two acute included angles. FIGS. 7, 7A, 10, 10A and 12, 12A show another "accordion fold" geometrical design which also lends itself to collapse. Also shown are various possible locations for the flashing 19. As shown in section, each of these variations can be viewed as having (with respect to the body) an axis of mirror symmetry along a medial portion thereof where the symmetry on either side thereof is generally of the shape of two facing truncated triangles facing one another with the apexes removed. This provides two parallel sidewalls interconnected by "V"-shaped sidewalls having a central narrow area allowing collapse because of the "accordion-like" narrowing. Similarly, FIGS. 8 and 13 illustrate another variation wherein instead of having the one "V"-shaped sidewall directed inwardly towards the other, it is pointed outwardly to provide an arrow-shaped contour. As before, the flashing 19 can be oriented along different parts of the body 4, FIG. 8 showing the flashing 19 as being centrally disposed and FIG. 13 showing the flashing as having one centrally disposed part and one adjacent a top wall 19. In view of the other examples, other variations on the flashing location should now be evident. FIG. 11 is a further variation in which the second of two "V"-shaped sidewalls have been replaced with a perpendicular wall and the flashing is located as shown in FIG. 13, but could of course be located elsewhere as described above. The key in all of these variations is that the body is provided with a means to encourage and promulgate collapse of the body in the presence of a force which causes the fluid contained within the body of the ampule 10 to be removed. By providing a body with a tendency to collapse, and by providing the robust interconnection between the outlet of the ampule with its docking to the coupling on the syringe, greater flexibility in manufacturing is possible and the tolerances of the wall thickness and plastic choice become greater. It is desired, however, that the seal that exists between the syringe and the ampule have a force which is greater than the force required to collapse the ampule so that no air is admitted between the interconnected syringe and ampule during the filling process of the syringe.

Figure 14:
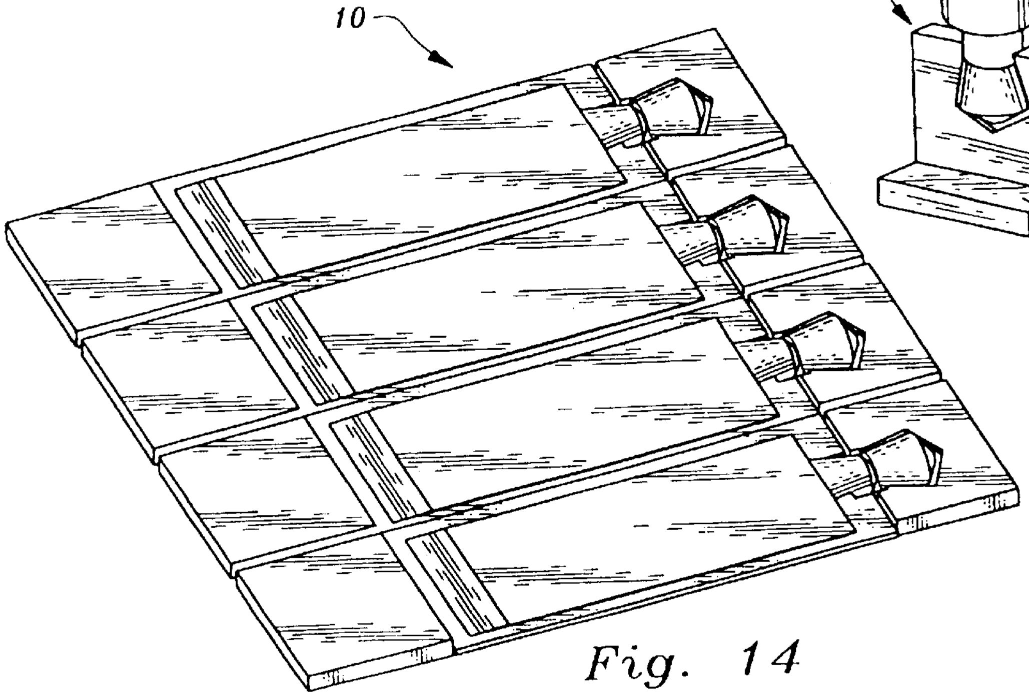
FIG. 14 is a perspective view of a series of ampules as they are produced and removed from blow-fill seal machine.

FIG. 14 shows a series of ampules as they would appear oriented in side by side relationship and interconnected by a thin membrane at junctures between adjacent ampules and made using a blow, fill, seal machine. The FIG. 14 series is based on the example with respect to FIGS. 6, 1 and 3.

FIG. 15 shows the syringe S standing on the cap 40 having a foot 46.

Moreover, having thus described the invention, it should be apparent that numerous structural modifications and adaptations may be resorted to without departing from the scope and fair meaning of the instant invention as set forth hereinabove and as defined hereinbelow by the claims.

I claim:

1. An ampule having a flexible collapsible body and further provided with means to promulgate said body's collapse in a certain area of said body and a cap connected to said body and an opening at a scoreline between said body and said cap;

wherein said opening has a cross-sectional area dimensioned to overlie an outlet on a dosing device;

wherein said means to promulgate said body's collapse includes a peripheral sidewall of said ampule formed with a zone which favors deformation upon the application of force;

wherein said zone of deformation further comprises an included angle between sides of said sidewall which is acute;

wherein said body of said ampule includes means adjacent said opening on an outer surface thereof which enhances the frictional connection between said opening and the dosing device;

wherein a seal exists at a juncture between the dosing device and said opening which device requires a force greater than said means to promulgate said body's collapse so that said body will collapse before said seal is broken;

wherein said ampule includes peripheral flashing circumscribing said body and cutouts are provided adjacent said opening; and including means to increase the strength of said seal between said opening and the dosing device comprising an inwardly directed radially extending biting edge at said opening which overlies the dosing device;

wherein said means to increase the sealing force between the dosing device and the body includes providing a bayonet type coupling on an outer surface of said ampule adjacent said opening.

2. An ampule having a flexible collapsible body and further provided with means to promulgate said body's collapse in a certain area of said body and a cap connected to said body and an opening at a scoreline between said body and said cap;

wherein said opening has a cross-sectional area dimensioned to overlie an outlet on a dosing device;

wherein said means to promulgate said body's collapse includes a peripheral sidewall of said ampule formed with a zone which favors deformation upon the application of force;

wherein said zone of deformation further comprises an included angle between sides of said sidewall which is acute;

wherein said body of said ampule includes means adjacent said opening on an outer surface thereof which enhances the frictional connection between said opening and the dosing device;

wherein a seal exists at a juncture between the dosing device and said opening; which device requires a force greater than said means to promulgate said body's collapse so that said body will collapse before said seal is broken;

wherein said ampule includes peripheral flashing circumscribing said body and cutouts are provided adjacent said opening; and including means to increase the strength of said seal between said opening and the dosing device comprising an inwardly directed radially extending biting edge at said opening which overlies the dosing device;

wherein said means to increase the sealing force includes a thread on an outer surface of said ampule adjacent said opening.

* * * * *